US010215695B1

(12) United States Patent
Farooq et al.

(10) Patent No.: US 10,215,695 B1
(45) Date of Patent: Feb. 26, 2019

(54) INSPECTION SYSTEM AND METHOD FOR DETECTING DEFECTS AT A MATERIALS INTERFACE

(71) Applicant: GLOBALFOUNDRIES INC., Grand Cayman (KY)

(72) Inventors: Mukta Farooq, Hopewell Junction, NY (US); Michael Shur, Vienna, VA (US)

(73) Assignee: GLOBALFOUNDRIES INC., Grand Cayman (KY)

(*) Notice: Subject to any disclaimer, the term of this patent is extended or adjusted under 35 U.S.C. 154(b) by 0 days.

(21) Appl. No.: 15/961,939

(22) Filed: Apr. 25, 2018

(51) Int. Cl.
*G01J 5/02* (2006.01)
*G01N 21/3581* (2014.01)
(Continued)

(52) U.S. Cl.
CPC ..... *G01N 21/3581* (2013.01); *G01N 21/3563* (2013.01); *G01N 21/8806* (2013.01); *G01N 21/9501* (2013.01); *G01N 2201/023* (2013.01); *G01N 2201/061* (2013.01); *G01N 2201/12* (2013.01)

(58) Field of Classification Search
CPC .............. G01N 21/94; G01N 21/3563; G01N 21/9505; G01N 21/95; G01N 21/3586; G01N 21/3577; G01N 2021/9513; G01N 21/3581; G01N 21/8806; G01N 21/9501; G01N 2201/023; G01N 2201/061; G01N 2201/12; G02F 1/1303; G02F 1/1309; G02F 2203/01; G02F 2203/02; G02F 2203/13; G02F 2203/69
See application file for complete search history.

(56) References Cited

U.S. PATENT DOCUMENTS 6,690,320 B2  2/2004  Benway et al.
7,619,263 B2  11/2009  Shur et al.
(Continued)

OTHER PUBLICATIONS

Dandolo et al., "Inspection of panel paintings beneath gilded finishes using terahertz time-domain imaging," Jun. 9-13, 2014, Papers from the Tenth Conference on Lasers in the Conservation of Artworks, pp. s-159 to s-166. (Year: 2014).*
(Continued)

*Primary Examiner* — Kiho Kim
(74) *Attorney, Agent, or Firm* — Gibb & Riley, LLC; Anthony J. Canale

(57) ABSTRACT

An inspection system and method that use a differential technique to accurately detect interface defects at a resolution on the order of tens of nanometers or less. Specifically, a radiation source (e.g., a THz or sTHz radiation source) is used to illuminate a materials interface within an object under test (e.g., a semiconductor wafer, integrated circuit (IC) chip package, etc.) under selectively varied inspection conditions. Suitable detector(s) are used to capture images of the materials interface when that interface is illuminated under the selectively varied inspection conditions. The captured images can be compared and contrasted to determine an actual differential in a property of the images. Based on this actual differential, a determination can be made as to whether or not the materials interface is defective and, particularly, as to whether or not the materials interface contains defects even defects that are a few nanometers or less in size.

20 Claims, 9 Drawing Sheets

(51) Int. Cl.
  *G01N 21/3563* (2014.01)
  *G01N 21/88* (2006.01)
  *G01N 21/95* (2006.01)

(56) References Cited

U.S. PATENT DOCUMENTS

| | | | |
|---|---|---|---|
| 7,955,882 B2 | 6/2011 | Shur et al. | |
| 9,310,417 B2 | 4/2016 | Chin et al. | |
| 2003/0025904 A1* | 2/2003 | Sakai | G01N 21/94 356/237.2 |
| 2011/0122403 A1* | 5/2011 | Jang | G01N 21/94 356/237.1 |
| 2015/0276375 A1* | 10/2015 | Liu | G01B 9/0203 356/511 |

OTHER PUBLICATIONS

Arnold et al., "Inspection of mechanical and electrical properties of silicon wafers using terahertz tomography and spectroscopy," 2015, Proceedings of SPIE, vol. 9483, pp. 94830w-1 to 94830w-6. (Year: 2015).*

Yamashita et al., "Imaging of Large-Scale Integrated Circuits Using Laser Terahertz Emission Microscopy," Optics Express, vol. 13, No. 1, 2005, pp. 115-120.

Kiwa et al., "Laser Terahertz Emission Microscope for Inspecting Electrical Faults in Integrated Circuits," Optics Letters, vol. 28, No. 21, 2003, pp. 2058-2060.

Stillman et at, "Sub-Terahertz Testing of Silicon MOSFET," Electronics Letters, vol. 44, Issue: 22, 2008, pp. 1-2.

Rumyantsev et at, "Terahertz Beam Testing of Millimeter Wave Monolithic Integrated Circuits," IEEE Sensors Journal, vol. 17, No. 17, 2017, p. 5487-5491.

Nagel et al., "Terahertz Imaging: Terahertz Reflectometry Images Faults in Silicon Chips," https://www.laserfocusworld.com/articles/print/volume-47/issue-11/features/terahertz-reflectometry-images-faults-in-silicon-chips.html, 2011, pp. 1-7.

* cited by examiner

INSPECTION SYSTEM AND METHOD FOR DETECTING DEFECTS AT A MATERIALS INTERFACE

BACKGROUND

Field of the Invention

The present invention relates to semiconductor wafer inspection and, more specifically, to inspection systems and methods for detecting defects at materials interfaces during integrated circuit manufacturing.

Description of Related Art

During integrated circuit manufacturing and packaging, inspections (referred to herein as process limiting yield (PLY) inspections) are typically performed in line after each process in order to detect defects of interest (DOI) (e.g., critical defects that have the potential to decrease yield). The DOIs can include, but are not limited to, voids, tears, shorts, etc. that occur at the interfaces between materials (referred to herein as interface defects). Such interface defects occur throughout manufacturing in the front end of the line (FEOL), middle of the line (MOL) and back end of the line (BEOL) from wafer bonding defects (e.g., voids between bonded wafer layers) to solder bump defects (e.g., white bumps). One exemplary technique that is currently used to detect such interface defects is time-domain reflectometry (TDR). With TDR, electrical signals are applied to an interface of interest (e.g., a pulse injection tip) and reflections of those signals are then captured (e.g., using a pulse detector tip). The waveforms of the reflected signals are then compared to the waveforms from a known good interface to determine if a defect is present at the materials interface. The resolution for TDR is, however, on the order of a few to 10 microns. Thus, smaller defects (e.g., on the order of a few nanometers) may be missed. Furthermore, TDR can lead to inaccurate or misleading results related to positioning of the tips as well as parasitic reflections.

SUMMARY

In view of the foregoing, disclosed herein are embodiments of an inspection system and method that uses a differential technique to accurately detect interface defects at a resolution on the order of tens of nanometers or less. Specifically, a radiation source (e.g., a terahertz (THz) or sub-terahertz (sTHz) radiation source) can be used to illuminate a materials interface within an object under test (e.g., in a semiconductor wafer, integrated circuit (IC) chip package, printed circuit board (PCB) assembly, etc.) under selectively varied inspection conditions. Suitable detector(s) (i.e., optical sensor(s)) can be used to capture images of the materials interface when that interface is illuminated under the selectively varied inspection conditions. The images can then be compared and contrasted to determine an actual differential in a property of the images. Based on this actual differential, a determination can be made as to whether or not the materials interface is defective and, particularly, as to whether or not the materials interface contains defects even defects that are a few nanometers or less in size.

More particularly, disclosed herein are embodiments of an inspection system. The inspection system can include various components including, but not limited to, a radiation source, at least one detector, an analyzer and a controller operably connected to the radiation source, detector(s) and analyzer. The radiation source can be a radiation source capable of generating and aiming beams of radiation toward an object under test in order to illuminate a materials interface (i.e., an interface between materials) contained within that object under test. The object under test can be, for example, a semiconductor wafer, an integrated circuit (IC) chip, an IC chip package, or a printed circuit board (PCB) assembly. The radiation can be within a range capable of passing through material(s) at least to, and optionally through, the materials interface. For example, the radiation from the radiation source can be within the terahertz (THz) or sub-terahertz (sTHz) range. The detector(s) can be optical sensor(s) suitable for capturing images of the materials interface when that interface is illuminated by (i.e., exposed to) the radiation.

During an inspection of the materials interface of the object under test, the controller can control the various system components and, optionally, the environmental conditions under which the inspection is performed in order to determine whether the materials interface is defective. Specifically, the controller can cause the radiation source to illuminate the materials interface with radiation under selectively varied inspection conditions and can further cause the detector(s) to capture at least two different images of the materials interface when the materials interface is illuminated under the selectively varied inspection conditions. The varied inspection conditions can include, but are not limited to, any of the following: different environmental conditions; different detector aperture settings; different relative locations of the radiation source, the detector(s) and the object under test; different primary beam intensities for the radiation; different primary beam frequencies for the radiation; and different primary beam directions for the radiation. The analyzer can then compare and contrast the different images to determine an actual differential in at least one property of the images and to further determine whether that materials interface is defective (i.e., whether the materials interface contains defect(s)), based on the actual differential.

Also disclosed herein are embodiments of an inspection method. The inspection method can include providing an inspection system that includes various components including, but not limited to, a radiation source, at least one detector, and an analyzer. The radiation source can be a radiation source capable of generating and aiming beams of radiation toward an object under test in order to illuminate a materials interface (i.e., an interface between materials) contained within that object under test. The object under test can be, for example, a semiconductor wafer, an integrated circuit (IC) chip, an IC chip package, or a printed circuit board (PCB) assembly. The radiation can be within a range capable of passing through material(s) at least to, and optionally through, the materials interface. For example, the radiation from the radiation source can be within the terahertz (THz) or sub-terahertz (sTHz) range. The detector(s) can be optical sensor(s) suitable for capturing images of the materials interface when that interface is illuminated by (i.e., exposed to) the radiation.

The inspection method can further include illuminating the materials interface with radiation under selectively varied inspection conditions, using the radiation source, and capturing at least two different images of the materials interface when the materials interface is illuminated under the selectively varied inspection conditions, using the detector(s). The varied inspection conditions can include, but are not limited to, any of the following: different environmental conditions; different detector aperture settings; different relative locations of the radiation source, the detector(s) and the object under test; different primary beam intensities for the radiation; different primary beam frequencies for the radiation; and different primary beam directions for the radiation. The inspection method can further include using the analyzer to compare and contrast the different images to determine an actual differential in at least one property of the images and to determine whether the materials interface is defective (i.e., whether the materials interface contains defect(s)), based on the actual differential.

Also disclosed herein is a computer program product. The computer program product can include a computer readable storage medium having program instructions embodied therewith. The program instructions can be readable by a computer and can cause the computer to perform the above-described method.

BRIEF DESCRIPTION OF THE SEVERAL VIEWS OF THE DRAWINGS

The present invention will be better understood from the following detailed description with reference to the drawings, which are not necessarily drawn to scale and in which.

DETAILED DESCRIPTION

Figure 1A:
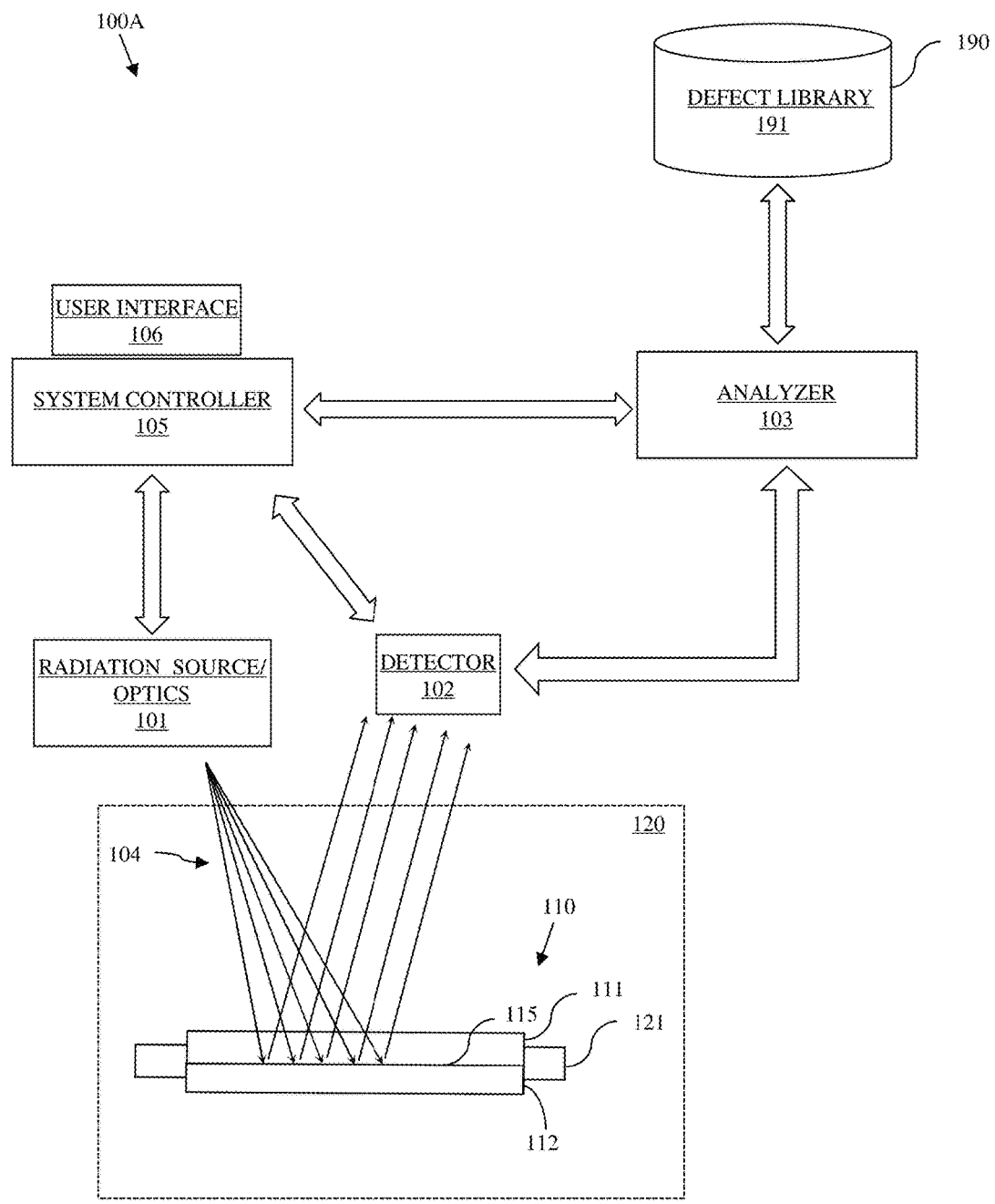
FIGS. 1A-1F are schematic diagrams illustrating embodiments of an inspection system.

As mentioned above, time-domain reflectometry (TDR) is one example of a technique that can be used to detect defects (e.g., voids, tears, shorts, etc.) at the interface between two materials. Unfortunately, the resolution for TDR is on the order of a few to 10 microns and, thus, TDR cannot be used to accurately detect smaller defects (e.g., defects on the order of a few nanometers). Furthermore, TDR can lead to inaccurate or misleading results related to positioning of the tips as well as parasitic reflections.

In view of the foregoing, disclosed herein are embodiments of an inspection system and method that uses a differential technique to accurately detect interface defects at a resolution on the order of tens of nanometers or less. Specifically, a radiation source (e.g., a terahertz (THz) or sub-terahertz (sTHz) radiation source) can be used to illuminate a materials interface within an object under test (e.g., in a semiconductor wafer, integrated circuit (IC) chip package, printed circuit board (PCB) assembly, etc.) under selectively varied inspection conditions. Suitable detectors(s) can be used to capture images of the materials interface when that interface is illuminated under the selectively varied inspection conditions. The images can then be compared and contrasted to determine an actual differential in a property of the images. Based on this actual differential, a determination can be made as to whether or not the materials interface is defective and, particularly, as to whether or not the materials interface contains defects even defects that are a few nanometers or less in size.

FIGS. 1A-1F show various different embodiments 100A-100F, respectively, of an inspection system, as disclosed herein. Generally, each of these embodiments 100A-100F includes at least a radiation source 101, one or more detectors 102, an analyzer 103 and a controller 105 that is operably connected to the radiation source 101, detector(s) 102 and analyzer 103. The radiation source 101 can be a radiation source capable of generating and aiming beams of radiation 104 toward an object under test 110 in order to illuminate a materials interface 115 (i.e., an interface between materials) contained within that object under test 110. The detector(s) 102 can be optical sensor(s) suitable for capturing images of the materials interface when that interface is illuminated by (i.e., exposed to) the radiation 104. During an inspection of the materials interface 115 of the object under test 110, the controller 105 can control the various other system components and, optionally, the environmental conditions under which the inspection is performed in order to determine whether the materials interface 115 is defective. Specifically, the controller 105 can cause the radiation source 101 to illuminate the materials interface 115 with radiation 104 under selectively varied inspection conditions and can further cause the detector(s) 102 to capture at least two different images of the materials interface 115 when the materials interface is illuminated under the selectively varied inspection conditions. The analyzer 103 can then compare and contrast the different images to determine an actual differential in at least one property of the images of the materials interface 115 at issue and to further determine whether that materials interface 115 is defective (i.e., whether the materials interface 115 contains defect(s)), based on the actual differential.

More particularly, each of the embodiments 100A-100F includes an object under test stage 120 for holding the object under test 110 during inspection, a radiation source 101, at least one detector 102, an analyzer 103 and a controller 105 operably connected to the object under test stage 120, the radiation source 101, the detector(s) 102, and the analyzer 103). Each of the embodiments 100A-100F of the inspection system can further include a user interface 106 adapted to allow a user to communicate with the controller 105 and set parameters for performing inspection operations.

The embodiments 100A-100F of the inspection system vary with regard to various optional features, as discussed in greater detail below. It should be understood that the figures and discussion thereof are not intended to be limiting and that multiple ones of these optional features may be incorporated into an embodiment not specifically illustrated.

In any case, the object under test 110 can be, for example, semiconductor wafer, an integrated circuit (IC) chip, an IC chip package, or a printed circuit board (PCB) assembly, or any other object under test that specifically has a first surface (e.g., front surface or front side), has a second surface (e.g., a back surface or back side), and contains at least one materials interface 115 to be inspected between the front surface and the back surface. The materials interface 115 to be inspected can be an interface 115 between a first material 111 and a second material 112 (i.e., an area where the first material is immediately adjacent to the second material). The first material 111 can be adjacent to the first surface and, more particularly, can be closer to the first surface than the second. The second material 112 can be adjacent to the second surface and, more particularly, can be closer to the second surface than the first. The first material 111 and the second material 112 can be different materials (i.e., made of different elements, compounds and/or alloys) or different layers of the same material. For example, the materials interface can be between a semiconductor layer (e.g., a silicon layer) and a dielectric layer (e.g., a silicon dioxide layer); between a semiconductor layer (e.g., a silicon layer) and a metal layer (e.g., a copper layer); between a dielectric layer (e.g., a silicon dioxide layer) and a metal layer (e.g., a copper layer); between a high-k dielectric layer and a work function metal layer; between two dielectric layers (e.g., a high-k dielectric layer and a silicon dioxide layer); between solder material and a metal pad; between an adhesive and a semiconductor substrate of a chip or PCB assembly; and so on.

Optionally, the outer surface (e.g., the front surface and the back surface) of the object under test 110 can be coated with a metamaterial film prior to the inspection process. Those skilled in the art will recognize that such a metal material film can be used to concentrate radiation 104 that will be used to illuminate the materials interface 115 during the inspection.

The object under test stage 120 can include a support frame 121 for supporting the object under test 110. The support frame 121 can be configured to hold and support the object under test 110 such that the radiation source 101 can direct radiation 104 toward the materials interface 115 (e.g., through the front surface of the object under test 110) and further such that detectors(s) 102 (i.e., optical sensor(s)) can capture (i.e., take, generate, produce, etc.) digital images of the materials interface 115 from the front surface (e.g., as illustrated in the embodiment 100A of FIG. 1A), from the back surface (e.g., as illustrated in the embodiment 100B of FIG. 1B) or from both the front surface and the back surfaces (e.g., as illustrated in the embodiment 100C of FIG. 1C), without interference from the support frame 121, when the object under test 110 is illuminated. For example, the support frame 121 can engage the outer edges of the object under test 110, leaving both the front and back surfaces of the object under test 110 exposed to the radiation 104 from the radiation source 101 and to the detector(s) 102.

Optionally, the support frame 121 in the object under test stage 120 can be a moveable support frame 121. In this case, the controller 105 can selectively control movement of the support frame 121 (e.g., in the X, Y and/or Z directions) and, thereby the position of the object under test 110 relative to the positions of the radiation source 101 and/or detector(s) 102 during the inspection. Such moveable supports are well known in the art and, thus, the details have been omitted from the specification in order to allow the reader to focus on the salient aspects of the disclosed systems.

Optionally, the object under test stage 120 can further include one or more means for selectively adjusting the environmental conditions of the object under test 110. For example, as illustrated in the embodiment 100D of FIG. 1D, the object under test stage 120 can include a heater 125. In this case, the controller 105 can selectively control the temperature of the heater 125 and, thereby the temperature of the object under test 110 during the inspection.

Figure 1B:
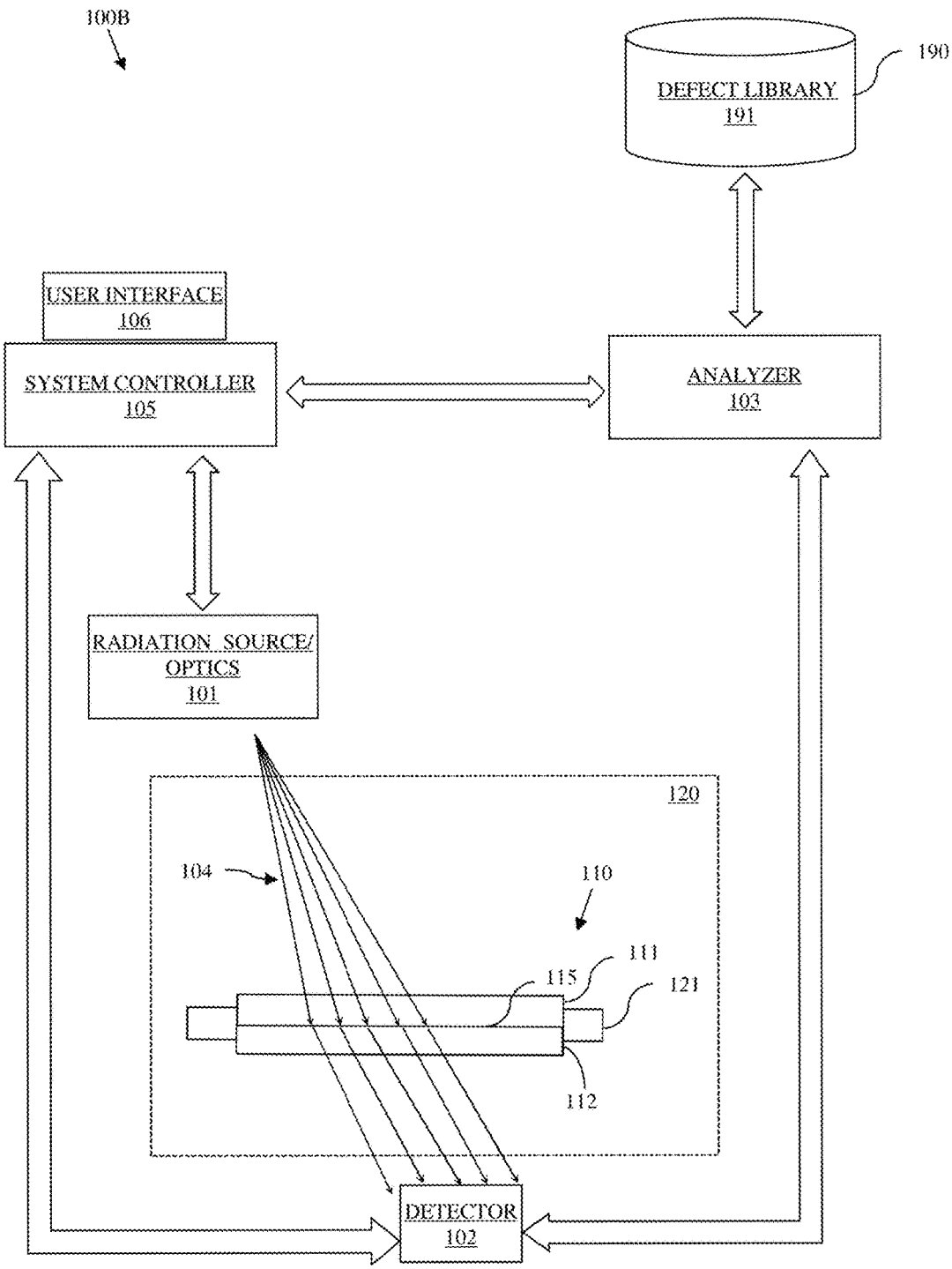
Figure 1C:
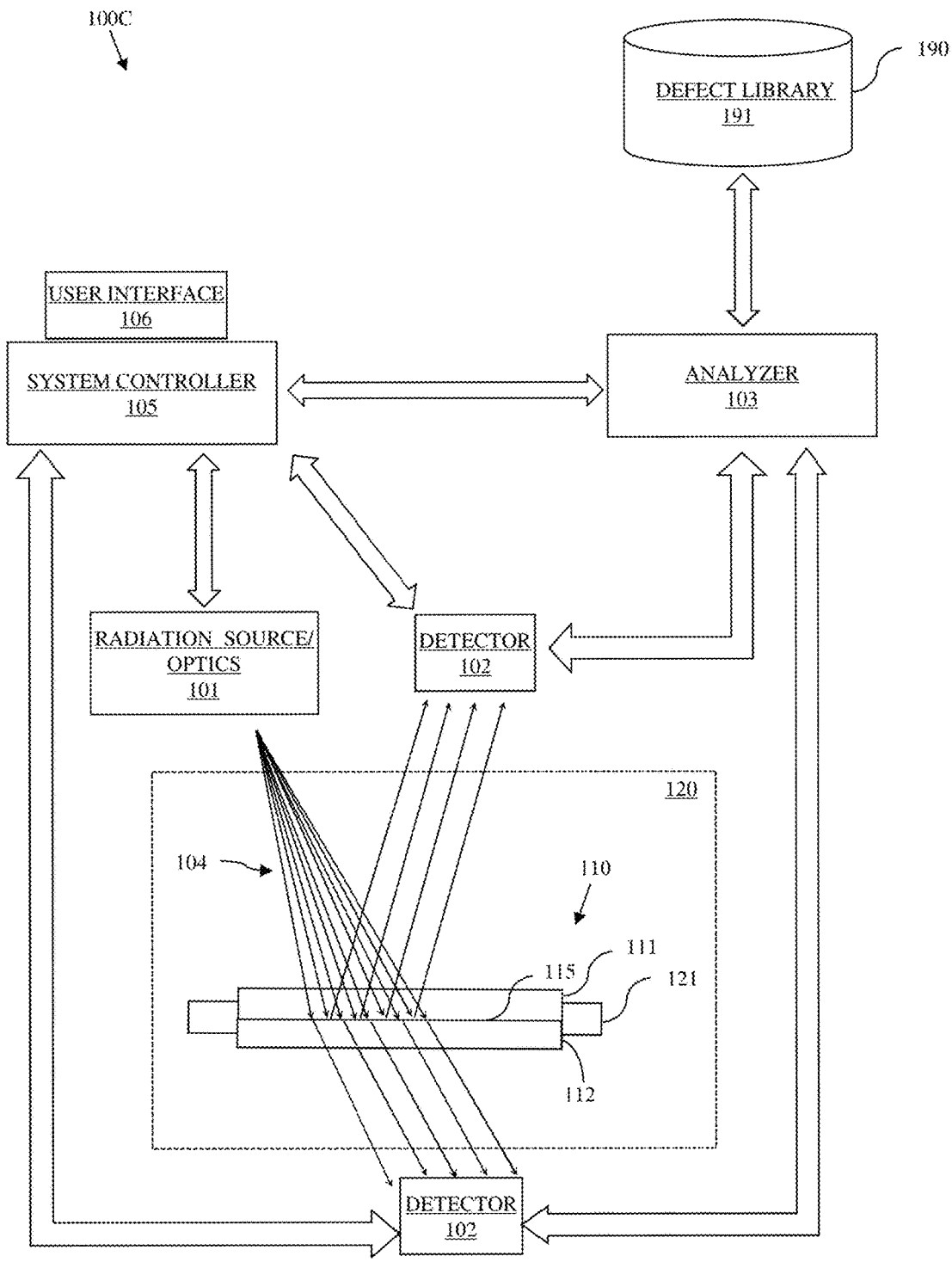
Figure 1D:
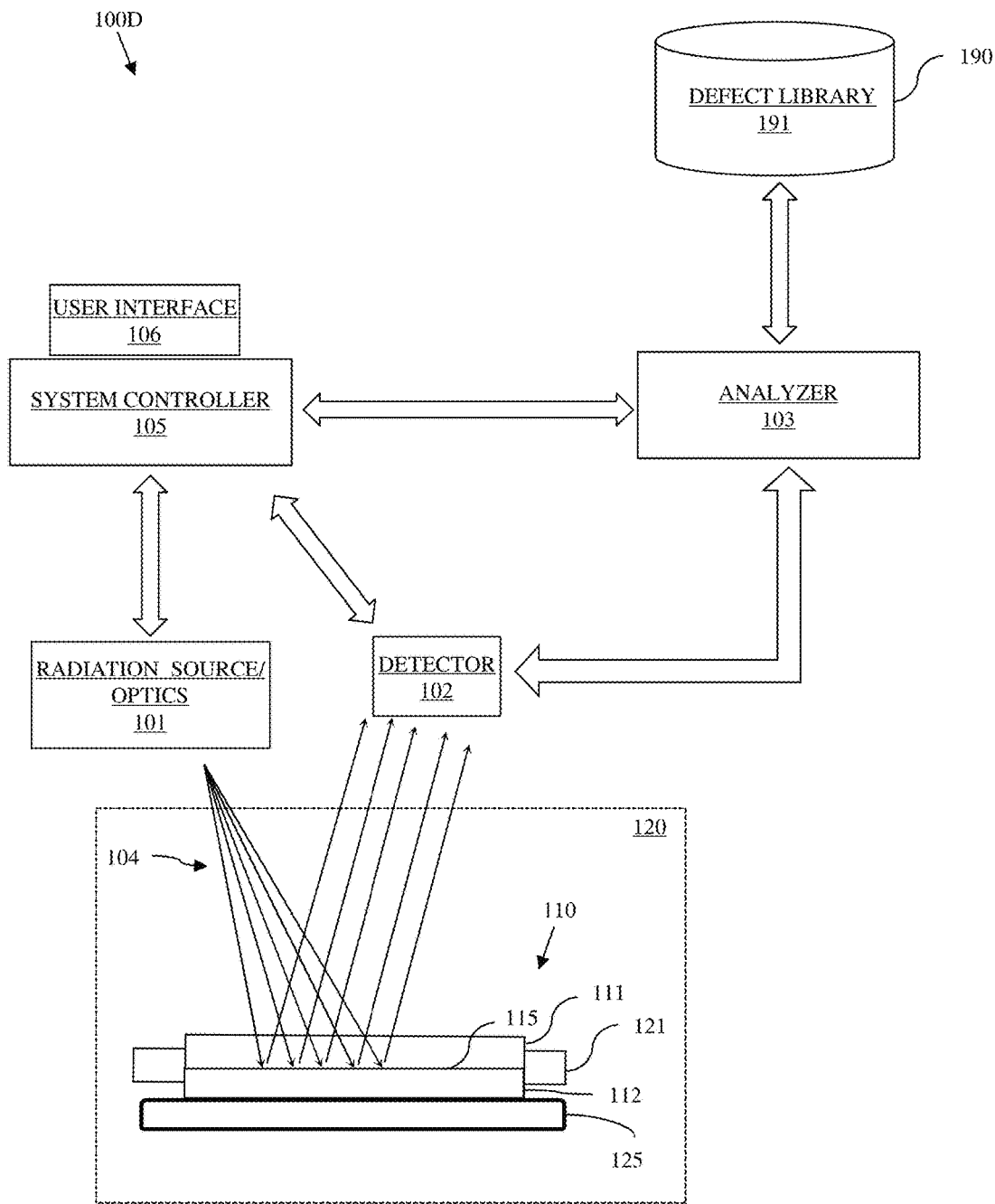
Figure 1E:
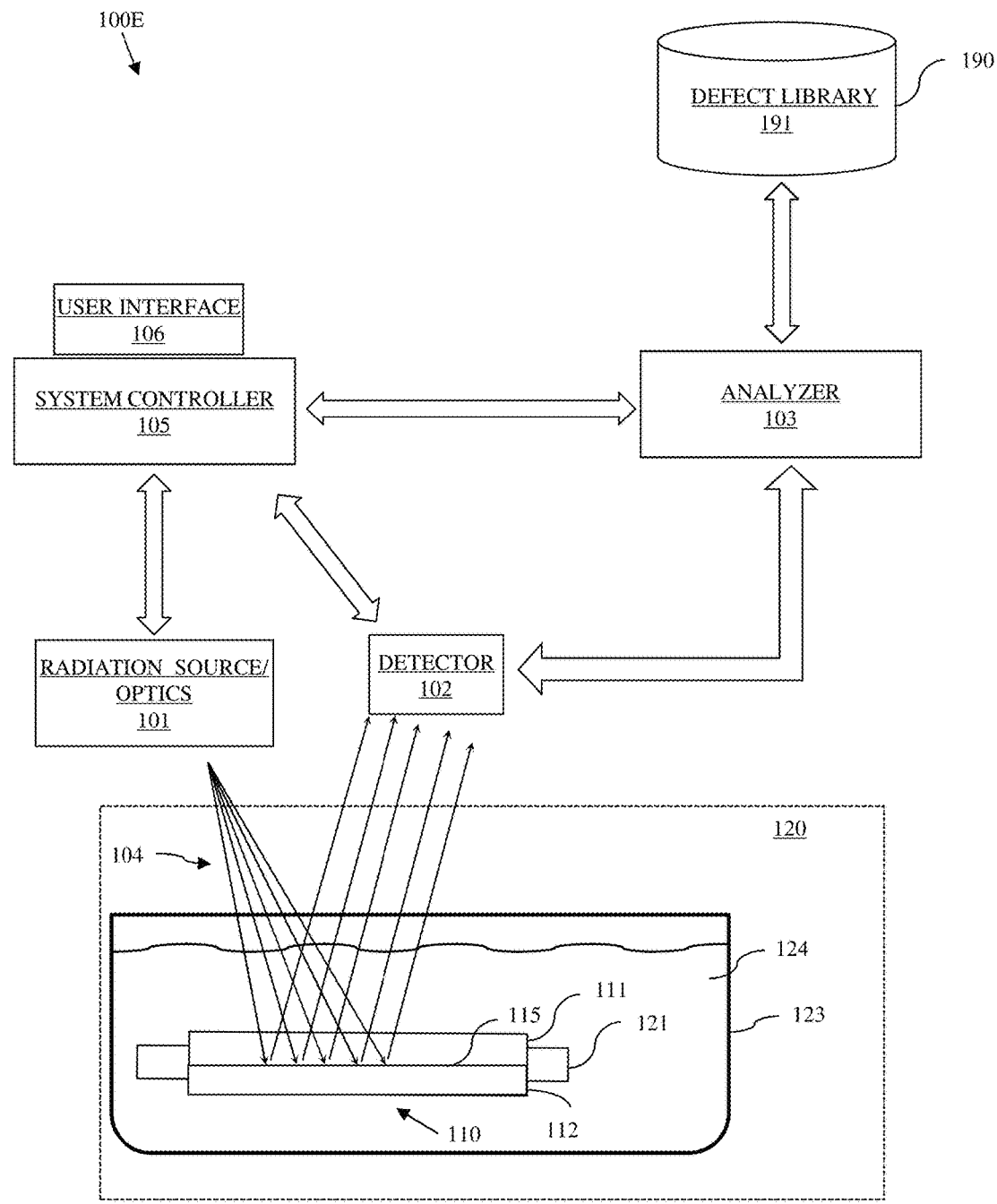

Optionally, the object under test stage 120 can further include a container 123 filled with a medium 124 within which the object under test 110 can be submerged during the inspection, as illustrated in the embodiment 100E of FIG. 1E). Submerging the object under test 110 within the medium 124 can be used to enhance the detection resolution by decreasing the wavelength of the radiation 104 reaching the materials interface 115 during the inspection.

The radiation source 101 (and corresponding optics) can be capable of generating and aiming beams of radiation 104 toward the object under test 110 in order to illuminate the materials interface 115. The radiation 104 can be within a range capable of passing through material(s) at least to, and optionally through, the materials interface. For example, the radiation 104 from the radiation source 101 can be within the terahertz (THz) or sub-terahertz (sTHz) range.

While the radiation source 101 would preferably generate and output radiation 104 at only one frequency (or wavelength), at only one intensity level, and aimed in only one direction (angled relative to a surface of the object under test 110), current state of the art radiation sources typically output radiation of multiple different frequencies (or wavelengths) within a given frequency range (or wavelength range), at multiple different intensities within a given intensity range, and aimed in multiple different directions within a given range of directions. In the embodiments disclosed herein, settings for radiation source 101 can be selectively controlled by the controller 105 to establish a primary beam frequency (or primary beam wavelength) at the midpoint of the frequency range, a primary beam intensity at the midpoint of the intensity range and a primary beam direction at the midpoint of beam direction range. In any case, the radiation source 101 can be positioned or otherwise adjusted so that beams of radiation 104 are generally aimed toward a given surface (e.g., a front surface) of the object under test 110 toward the materials interface 115 within the object under test 110.

Optionally, the radiation source 101 can be supported by a moveable support means (not shown). In this case, the controller 105 can selectively control movement of the support means (e.g., in the X, Y and/or Z direction) and, thereby the position of the radiation source 101 relative to the positions of the object under test 110 and/or detector(s) 102 during the inspection. Such moveable supports are well known in the art and, thus, the details have been omitted from the specification in order to allow the reader to focus on the salient aspects of the disclosed systems.

The detector(s) 102 can be optical sensor(s) suitable for capturing images of the materials interface 115 when that interface is illuminated by (i.e., exposed to) the radiation 104. For example, if the radiation 104 is within the terahertz (THz) or sub-terahertz (sTHz) range, the detector(s) 102 can be THz or sTHz detectors capable of registering radiation in the same frequency range. Furthermore, the detector(s) 102 can be pixelated or pixelless detector(s).

In any case, the detector(s) 102 can be supported by support means (not shown) and positioned adjacent to a surface of object under test 110 to enable capturing of an image of the materials interface 115 when that interface is illuminated. For example, as illustrated in the embodiment 100A of FIG. 1A, a detector 102 can be positioned at a location on the same side of the object under test as the radiation source 101 (e.g., adjacent to the front surface) and can capture an image by detecting radiation reflected off of the materials interface 115 when the object under test is illuminated. Alternatively, as illustrated in the embodiment 100B of FIG. 1B, a detector 102 can be positioned at a location on the opposite side of the object under test as the radiation source 101 (e.g., adjacent to the back surface) and can capture an image by detecting radiation transmitted through the materials interface 115 when the object under test is illuminated. Alternatively, as illustrated in the embodiment 100C of FIG. 1C, a pair of detectors 102 can be positioned at locations on both side of the object under test as and can capture images by detecting both radiation reflected off the materials interface and radiation transmitted through the materials interface 115 when the object under test is illuminated.

Optionally, each detector 102 can be supported by a moveable support means (not shown). In this case, the controller 105 can selectively control movement of the support means (e.g., in the X, Y and/or Z direction) and, thereby the position of the detector relative to the object under test 110 and/or the radiation source 101 during the inspection. For example, the detector could be moved closer to or further away from the surface of the object under test and/or could be moved in various directions scanning along the surface of the object under test 110. Such moveable supports are well known in the art and, thus, the details have been omitted from the specification in order to allow the reader to focus on the salient aspects of the disclosed systems.

Optionally, the detector(s) 102 can each have an aperture the size of which is selectively adjustable. Those skilled in the art will recognize that the aperture is the maximum diameter of the opening through which light passes in the detector optics. In this case, the controller 105 can selectively control the size of the aperture. Preferably, the detector aperture can be adjusted so as to be smaller than the wavelength of the radiation (i.e., so as to be a sub-wavelength aperture). As a result, the defect detection resolution can be relatively small (e.g. on the order of a few nanometers).

During an inspection of the materials interface of the object under test 110, the controller 105 can control the various system components described above and, optionally, the environmental conditions under which the inspection is performed in order to determine whether the materials interface is defective. Specifically, the controller 105 (based on user inputs entered through the user interface 106) can cause the radiation source 101 to illuminate the materials interface 115 with radiation 104 under selectively varied inspection conditions and can further cause the detector(s) 102 to capture at least two different images of the materials interface 115 when the materials interface 115 is illuminated under the selectively varied inspection conditions.

It should be noted that the images could be two-dimensional images. Alternatively, for each image multiple different intensities of THz or sTHz radiation could be used to penetrate to different depths within the object under test 110 (e.g., within increasing penetration depths corresponding to the different radiation intensities), thereby allowing for the creation of three-dimensional images.

The varied inspection conditions can include, for example, different relative locations of the radiation source 101, the detector(s) 102 and the object under test 110.

For example, referring to the embodiment 100A shown in FIG. 1A, the controller 105 can cause beams of radiation 104 to be directed into the first surface (e.g., the front surface) of the object under test 110. Given the materials used and the settings for the beams from the radiation source (e.g., primary beam frequency or wavelength, the primary beam angle, the primary beam intensity, etc.), the beams of radiation can pass through the first material 111, be reflected off the second material 112 at the materials interface 115, and can exit back out the first surface of the object under test 110. During this illumination process, a single detector 102, which is positioned at a given location adjacent to the first surface, can capture a first image of the materials interface 115. Then, the location of the detector 102 can be adjusted relative to the first surface (e.g., in the X, Y and/or Z direction by movement of the detector and/or the object under test) and the detector 102 can capture a second image of the materials interface 115. Optionally, the relative positions of the detector and the object under test can be adjusted multiple times to capture multiple different images from the same side of the object under test when the materials interface is illuminated.

Alternatively, referring to the embodiment 100B shown in FIG. 1B, the controller 105 can cause beams of radiation 104 to be directed into the first surface (e.g., the front surface) of the object under test 110. However, in this case, given the materials used and the settings for the beams from the radiation source (e.g., primary beam frequency or wavelength, the primary beam angle, the primary beam intensity, etc.), the beams of radiation can pass through the first material 111, through the materials interface 115, through the second material 112 and can exit out the second surface (e.g., the back surface) of the object under test 110. During this illumination process, a single detector 102, which is positioned at a given location adjacent to the second surface, can capture a first image of the materials interface 115. Then, the location of the detector 102 relative to the object under test can be adjusted relative to the second surface (e.g., in the X, Y and/or Z direction by movement of the detector and/or the object under test) and the detector 102 can capture a second image of the materials interface 115. Optionally, the relative positions of the detector and the object under test can be adjusted multiple times to capture multiple different images from the same side of the object under test when the materials interface is illuminated.

Alternatively, referring to the embodiment 100C shown in FIG. 1C, the controller 105 can cause beams of radiation 104 to be directed into the first surface (e.g., the front surface) of the object under test 110. However, in this case, given the materials used and the settings for the beams from the radiation source (e.g., primary beam frequency or wavelength, the primary beam angle, the primary beam intensity, etc.), a first portion of the beams of radiation passes through the first material 111, is reflected off the second material 112 at the materials interface 115, and exits back out the first surface of the object under test 110, while a second portion passes through the first material 111, through the materials interface 115, through the second material 112 and exits out the second surface (e.g., the back surface) of the object under test 110. During this illumination process, multiple detectors located on opposite sides of the object under test can capture the required images. For example, one detector 102, which is positioned at a first location adjacent to the first surface, can capture a first image of the materials interface 115 and another detector 102, which is positioned at a second location adjacent to the second surface, can capture a second image of the materials interface 115. Optionally, the relative positions of the detectors and the object under test can be adjusted multiple times to capture multiple different images from the same side of the object under test when the materials interface is illuminated.

Additionally or alternatively, the varied inspection conditions can include, for example, different detector aperture settings. As mentioned above, the detector(s) 102 in any of the embodiments can have apertures the size of which can be selectively adjusted. Those skilled in the art will recognize that the aperture is the maximum diameter of the opening through which light passes in the detector optics. In this case, the multiple different images can be captured using multiple different aperture sizes, respectively. Ideally, the aperture sizes will be sub-wavelength aperture sizes (i.e., smaller than the wavelength of the radiation 104).

Additionally or alternatively, the varied inspection conditions can include, for example, different environmental conditions. For example, as illustrated in the embodiment 100D of FIG. 1D, the object under test stage 120 can include a heater 125. In this case, the multiple different images can be captured using multiple temperature settings, respectively, on the heater 125. Also, for example, as illustrated in the embodiment 100E of FIG. 1E, the object under test stage 120 can include a container 123, which can hold a medium 124 within which the object under test 110 can be submerged. In this case, the multiple different images can be captured both with and without submerging the object under test 110 in a medium or can be captured when submerging the object under test in different media. As mentioned above, submerging the object under test 110 within the medium 124 can be used to enhance the detection resolution by decreasing the wavelength of the radiation 104 reaching the materials interface 115 during the inspection. It should be understood that the environmental conditions mentioned herein are not intended to be limiting. Additionally or alternatively, the object under test stage 120 could be configured to subject the object under test to any number of different environmental conditions (e.g., different pressure environments, different gas environments, etc.).

Additionally or alternatively, the varied inspection conditions can include different settings to be used by the radiation source 101 resulting in, for example, any of the following: different primary beam intensities for the radiation 104; different primary beam frequencies (or wavelengths) for the radiation 104; different primary beam directions for radiation 104; etc.

The analyzer 103 can then compare and contrast the different images captured by the detector(s) 102 to determine an actual differential in at least one property of the images of the materials interface 115 at issue and to determine whether that materials interface 115 is defective (i.e., whether the materials interface 115 contains defect(s)) and, optionally, to identify any defects by type based on the actual differential.

Specifically, the actual differential can be, for example, actual image intensity differences between the images at the same location on the materials interface 115. Those skilled in the art will recognize that image intensity refers to brightness or darkness and is dependent upon the size of the aperture used. The actual differential can be, for example, image color (or gray scale) differences between the images at the same location on the materials interface 115. The actual differential can be, for example, spectral response differences between the images at the same location on the materials interface 115. Those skilled in the art will recognize that a spectral response pattern refers to the magnitude of energy that an object reflects or emits across a range of wavelengths. Alternatively, the actual differential can be any other suitable measurable differential between the images at the same location on the materials interface 115.

Based on the actual differential, the analyzer 103 can determine if the materials interface 115 is defective. That is, the analyzer 103 can determine if the materials interface 115 contains defect(s) at specific locations on the materials interface 115.

For example, each embodiment 100A-100F of the inspection system can further include a memory 190, which is accessible by the analyzer 190, and a defect library 191, which is stored within the memory 190. The defect library 191 can list multiple interfaces by type and, specifically, by the two materials positioned immediately adjacent to each other at the materials interface. Furthermore, for each interface, the defect library 191 can indicate the following: a particular condition variation used during inspection and an expected differential (if any) in a property of the images of the materials interface 115, which will indicate that the materials interface is non-defective when the inspection is performed using the particular condition variation.

The analyzer 190 can compare the actual differential to an expected differential stored in the library and associated with the materials interface at issue in order to determine whether the materials interface 115 is defective (i.e., whether the materials interface contains any defects). When the actual differential and the expected differential are essentially the same across the images, then a determination can be made that the materials interface is non-defective. However, if the actual differential and the expected differential are different (e.g., by some threshold amount) at the same location within the images, then a determination can be made that the materials interface contains at that location.

Figure 2A:
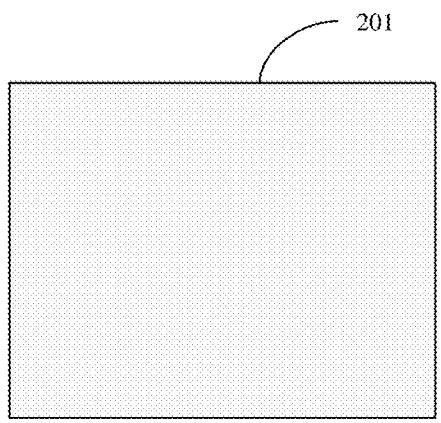
FIGS. 2A and 2B depict two different images of a non-defective materials interface captured under different conditions.
Figure 2B:
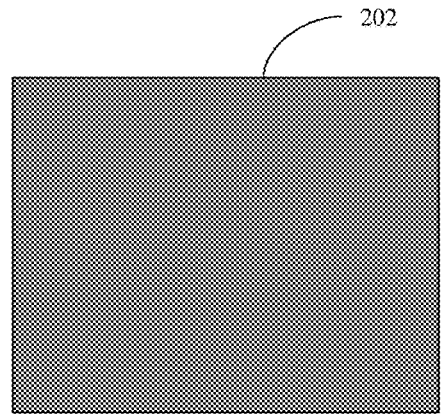

For example, FIGS. 2A and 2B depict two different images 201 and 202, respectively, of a specific non-defective materials interface (e.g., a non-defective silicon to silicon dioxide interface or any other specific materials interface), wherein the two different images 201-202 were captured using selectively varied conditions (e.g., a first sub-wavelength aperture (see FIG. 2A) and a second sub-wavelength aperture that is smaller than the first sub-wavelength aperture (see FIG. 2B)). As a result, the two different images 201 and 202 have different image intensity levels (i.e., different brightness levels). That is, these FIGS. 2A and 2B show the expected image intensity level differential between two different images 201 and 202 of a non-defective materials interface when a particular conditions variation is applied when capturing the images. In this case, the smaller aperture used to capture the image 202 results in the image 202 being darker than the image 201.

Figure 3A:
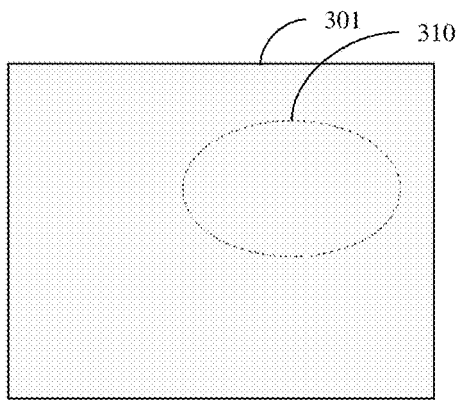
FIGS. 3A and 3B depict two different images of a defective materials interface captured under different conditions.
Figure 3B:
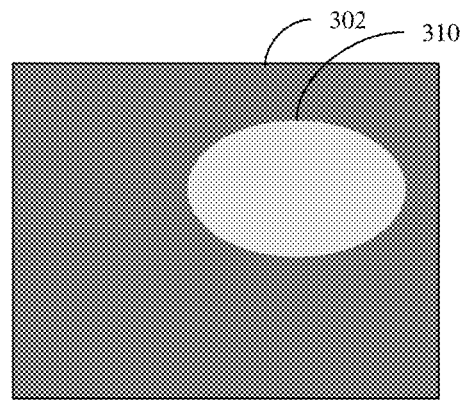

FIGS. 3A and 3B depict two different images 301 and 302, respectively, of the same materials interface when the interface has a defect (i.e., a defective area 310). Specifically, as with the images 201 and 202, the images 301 and 302 were captured using the selectively varied conditions (e.g., a first sub-wavelength aperture (see FIG. 3A) and a second sub-wavelength aperture that is smaller than the first sub-wavelength aperture (see FIG. 3B)). As a result, the two different images 301 and 302 have different image intensity levels (i.e., different brightness levels). However, within one particular area 310 on the materials interface 115, the actual differential in the image intensity levels between the two different images 301 and 302 is significantly different from the expected differential (in this case, much less than expected). This unexpected differential indicates that there is a defect within the area 310. That is, the fact that the brightness level of the area 310 did not change as expected between the image 301 and the image 302 (i.e., did not change in the same way as the rest of the material surface between the image 301 and the image 302) raises the likelihood that area 310 contains a defect (i.e., that this area is a defective area).

Optionally, the analyzer 103 can further identify any detected defects by type (e.g., void, short, tear, etc.). For example, for each materials interface inspected under a particular conditions variation, the defect library 191 can further associate at least one threshold difference between the expected differential and the actual differential with a specific defect type. In this case, the analyzer 103 can further determine a value of the difference between the expected differential and the actual difference and can compare that value to a threshold difference in order to identify the defect by type. For example, a particular conditions variation can be a decrease in aperture size by, for example, 50% between the first image and the second image; an expected differential in image intensity between the two images can be, for example, a 50% decrease, and a threshold difference for detecting a void can be, for example, a difference of 10 points or more. In this case, if the actual differential in image intensity between the two images is less than 40%, then a defect can be detected and that defect can be identified as a void. It should be understood that this is just one example and it is not intended to be limiting. Other types of defects would result in different characteristic changes in imaging at the materials interface and those characteristic changes would vary depending upon the conditions variations used when the images are taken.

Figure 1F:
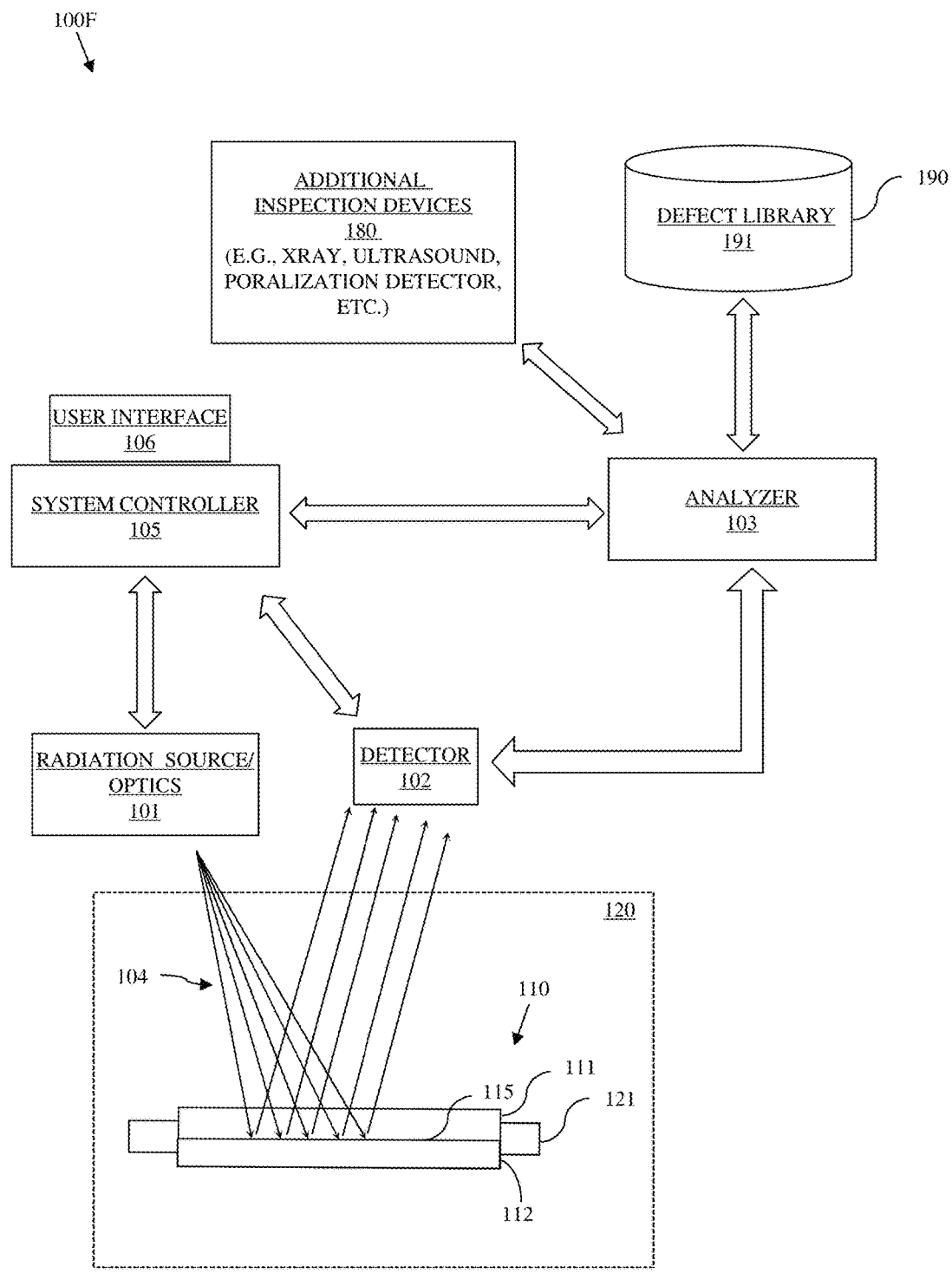

Optionally, as illustrated in the embodiment 100F of FIG. 1F, the analyzer 103 can further be in communication with one or more additional inspection devices 180 that perform additional inspection processes or the memory (or memories) that store the results of such additional inspection processes. Additional inspection devices 180 can include, but are not limited to, any one or more of the following: a polarization detector (which is adapted to detect the polarization of radiation), an X-ray device (which is adapted to capture X-ray images), and an ultrasound device (which captures ultrasound images). The additional inspection processes can be conventional inspection processes performed using these devices to detect and identify defects. The results of any additional inspection process can be considered by the analyzer 103 to ensure the accuracy any defect detection and/or identification. Alternatively, the additional inspection devices can capture different images under selectively varied inspection conditions. For example, during an inspection, the polarization detector can capture at least two different polarization images of radiation (e.g., THz or sTHz radiation) that is emitted from the materials interface under selectively varied inspections conditions. Additionally or alternatively, during an inspection, an X-ray device can be used to capture at least two different X-ray images of the materials interface under selectively varied inspection conditions. Additionally or alternatively, during an inspection, an ultrasound device can be used to capture at least two different ultrasound images of the materials interface under selectively varied inspection conditions. In any case, for the different images captured by each additional inspection device, an actual differential in a property of the images can be determined and compared to an expected differential (stored in the defect library 191) in order to further assist in the determination of whether the materials interface at issue is defective and, if so, to further assist in the identification of the defect by type.

It should be noted that the information, which is stored within the defect library 191 (i.e., information associated with specific materials interfaces and with particular conditions variations used during inspection of those specific materials interfaces) could be empirically determined or, alternatively, determined through simulations. Furthermore, it is anticipated that, as more and more different materials interfaces are inspected under more and more different selectively varied inspection conditions, the defect library 191 will be updated to provide for improved defect detection and identification capabilities.

Finally, in the exemplary system embodiments described above, inspection of only a single materials interface within an object under test is discussed. However, it should be understood that similar techniques may also be used to simultaneously inspect multiple parallel interfaces and/or in multiple intersecting interfaces, particularly when three-dimensional images are used.

Figure 4:
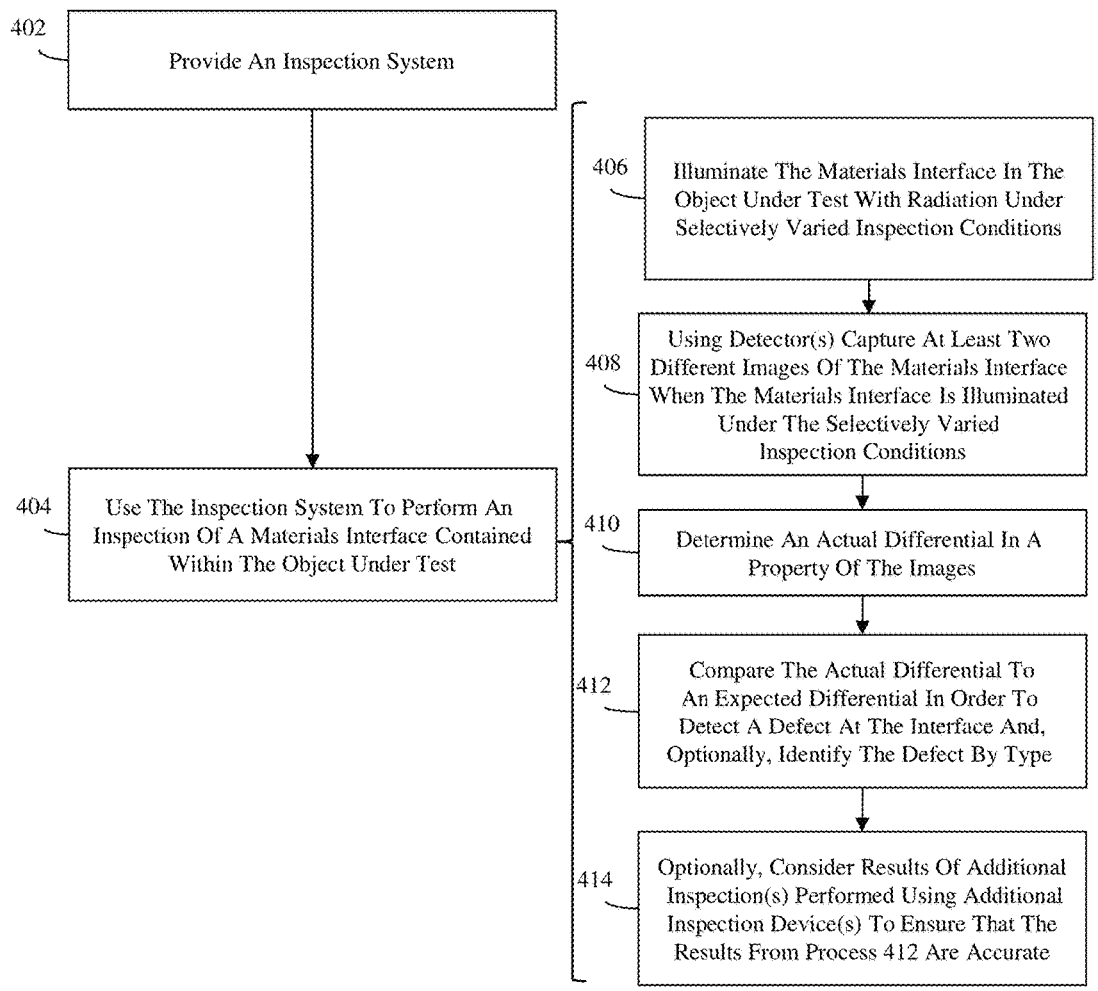
FIG. 4 is a flow diagram illustrating an inspection method.

FIG. 4 is a flow diagram illustrating an inspection method. This inspection method can include providing an inspection system, such as the inspection system described above, which includes at least a radiation source 101, one or more detectors 102, an analyzer 103 (which has access to a defect library 191) and a controller 105 that is operably connected to the radiation source 101, detector(s) 102 and analyzer 103 (see process 402 and inspection system embodiments 100A-100F of FIGS. 1A-1F, described in detail above). This inspection method can further include using the inspection system provided at process 402 to perform an inspection of a materials interface 115, which is contained within an object under test 110 (see process 404).

Specifically, the process 404 of inspecting a materials interface 115 within an object under test 110 can include using a radiation source 101 to illuminate the materials interface 115 with radiation 104 under selectively varied inspection conditions (see process 406) and further using detector(s) 102 to capture at least two different images of the materials interface 115 when that interface is illuminated under the selectively varied inspection conditions, using the detector(s) 102 (see process 408). The process 404 of inspecting the materials interface 115 can further include comparing and contrasting the different images captured at process 408 to determine an actual differential in at least one property of the images of the materials interface 115 at issue and, based on the actual differential, to determine whether the materials interface 115 is defective (i.e., whether the materials interface 115 contains defect(s)) and, if so, to optionally identify any defects by type.

More specifically, the object under test 110 can be, for example, semiconductor wafer, an integrated circuit (IC) chip, an IC chip package, or a printed circuit board (PCB) assembly, or any other object under test that has a first surface (e.g., front surface or front side), has a second surface (e.g., a back surface or back side), and contains at least one materials interface 115 to be inspected between the front surface and the back surface. The materials interface 115 to be inspected can be an interface 115 between a first material 111 and a second material 112 (i.e., an area where the first material is immediately adjacent to the second material). The first material 111 can be adjacent to the first surface and, more particularly, can be closer to the first surface than the second. The second material 112 can be adjacent to the second surface and, more particularly, can be closer to the second surface than the first. The first material 111 and the second material 112 can be different materials (i.e., made of different elements, compounds and/or alloys) or different layers of the same material. For example, the materials interface can be between a semiconductor layer (e.g., a silicon layer) and a dielectric layer (e.g., a silicon dioxide layer); between a semiconductor layer (e.g., a silicon layer) and a metal layer (e.g., a copper layer); between a dielectric layer (e.g., a silicon dioxide layer) and a metal layer (e.g., a copper layer); between a high-k dielectric layer and a work function metal layer; between two dielectric layers (e.g., a high-k dielectric layer and a silicon dioxide layer); between solder material and a metal pad; between an adhesive and a semiconductor substrate of a chip or PCB assembly; and so on. Optionally, the outer surface (e.g., the front surface and the back surface) of the object under test 110 can be coated with a metamaterial film prior to the inspection process. Those skilled in the art will recognize that such a metal material film can be used to concentrate radiation 104 that will be used to illuminate the materials interface 115 during the inspection.

As mentioned above, the process 404 of inspecting the materials interface 115 within the object under test 110 can include illuminating the materials interface 115 with radiation 104 (e.g., from the radiation source 101) under selectively varied inspection conditions (see process 406) and capturing at least two different images of the materials interface 115 (e.g., using detector(s) 102) when the materials interface 115 is illuminated under the selectively varied inspection conditions (see process 408). The radiation 104 can be within a range capable of passing through material(s) at least to, and optionally through, the materials interface. For example, the radiation 104 from the radiation source 101 can be within the terahertz (THz) or sub-terahertz (sTHz) range. Furthermore, if the radiation 104 is within the terahertz (THz) or sub-terahertz (sTHz) range, the detectors(s) 102 can be THz or sTHz optical sensors capable of registering radiation in the same frequency range. Furthermore, the detector(s) 102 can be pixelated or pixelless detector(s).

It should be noted that the images could be two-dimensional images. Alternatively, for each image multiple different intensities of THz or sTHz radiation could be used to penetrate to different depths within the object under test 110 (e.g., within increasing penetration depths corresponding to the different radiation intensities), thereby allowing for the creation of three-dimensional images.

The varied inspection conditions used at processes 406-408 can include, for example, different relative locations of the radiation source 101, the detector(s) 102 and the object under test 110.

For example, beams of radiation 104 can be directed into the first surface (e.g., the front surface) of the object under test 110 (see the inspection system embodiment 100A of FIG. 1A). Given the materials used and the settings for the beams from the radiation source (e.g., primary beam frequency or wavelength, the primary beam angle, the primary beam intensity, etc.), the beams of radiation can pass through the first material 111, be reflected off the second material 112 at the materials interface 115, and can exit back out the first surface of the object under test 110. During this illumination process, a single detector 102, which is positioned at a given location adjacent to the first surface, can capture a first image of the materials interface 115. Then, the location of the detector 102 can be adjusted relative to the first surface (e.g., in the X, Y and/or Z direction by movement of the detector and/or the object under test) and the detector 102 can capture a second image of the materials interface 115. Optionally, the relative positions of the detector and the object under test can be adjusted multiple times to capture multiple different images from the same side of the object under test when the materials interface is illuminated.

Alternatively, beams of radiation 104 can be directed into the first surface (e.g., the front surface) of the object under test 110 (e.g., see the inspection system embodiment 100B of FIG. 1B). However, in this case, given the materials used and the settings for the beams from the radiation source (e.g., primary beam frequency or wavelength, the primary beam angle, the primary beam intensity, etc.), the beams of radiation can pass through the first material 111, through the materials interface 115, through the second material 112 and can exit out the second surface (e.g., the back surface) of the object under test 110. During this illumination process, a single detector 102, which is positioned at a given location adjacent to the second surface, can capture a first image of the materials interface 115. Then, the location of the detector 102 relative to the object under test can be adjusted relative to the second surface (e.g., in the X, Y and/or Z direction by movement of the detector and/or the object under test) and the detector 102 can capture a second image of the materials interface 115. Optionally, the relative positions of the detector and the object under test can be adjusted multiple times to capture multiple different images from the same side of the object under test when the materials interface is illuminated.

Alternatively, beams of radiation 104 can be directed into the first surface (e.g., the front surface) of the object under test 110 (see the inspection system embodiment 100C of FIG. 1C). However, in this case, given the materials used and the settings for the beams from the radiation source (e.g., primary beam frequency or wavelength, the primary beam angle, the primary beam intensity, etc.), a first portion of the beams of radiation passes through the first material 111, is reflected off the second material 112 at the materials interface 115, and exits back out the first surface of the object under test 110, while a second portion passes through the first material 111, through the materials interface 115, through the second material 112 and exits out the second surface (e.g., the back surface) of the object under test 110. During this illumination process, multiple detectors located on opposite sides of the object under test can capture the required images. For example, one detector 102, which is positioned at a first location adjacent to the first surface, can capture a first image of the materials interface 115 and another detector 102, which is positioned at a second location adjacent to the second surface, can capture a second image of the materials interface 115. Optionally, the relative positions of the detectors and the object under test can be adjusted multiple times to capture multiple different images from the same side of the object under test when the materials interface is illuminated.

Additionally or alternatively, the varied inspection conditions used at process 406-408 can include, for example, different detector aperture settings. As mentioned above, the detector(s) 102 in any of the inspection system embodiments can have apertures the size of which can be selectively adjusted. In this case, the multiple different images can be captured using multiple different aperture sizes, respectively. Ideally, the aperture sizes will be sub-wavelength aperture sizes (i.e., smaller than the wavelength of the radiation 104).

Additionally or alternatively, the varied inspection conditions used at processes 406-408 can include, for example, different environmental conditions. For example, the multiple different images can be captured using multiple temperature settings, respectively, on a heater 125 (e.g., see the inspection system embodiment 100D of FIG. 1D). Also, for example, the multiple different images can be captured both with and without submerging the object under test 110 in a medium or can be captured when submerging the object under test in different media (e.g., as illustrated in the inspection system embodiment 100E of FIG. 1E). As mentioned above, submerging the object under test 110 within a medium 124 can be used to enhance the detection resolution by decreasing the wavelength of the radiation 104 reaching the materials interface 115 during the inspection. It should be understood that the environmental conditions mentioned herein are not intended to be limiting. Additionally or alternatively, the object under test could be subjected to any number of different environmental conditions (e.g., different pressure environments, different gas environments, etc.).

Additionally or alternatively, the varied inspection conditions used at processes 406-408 can include different settings to be used by the radiation source 101 resulting in, for example, any of the following: different primary beam intensities for the radiation 104; different primary beam frequencies (or wavelengths) for the radiation 104; different primary beam directions for radiation 104; etc.

Additionally, during an inspection of the materials interface 115 of the object under test 110, the different images captured by the detector(s) 102 can be compared and contrasted (e.g., by the analyzer 103) to determine an actual differential in at least one property of the images of the materials interface 115 at issue (see process 410). The actual differential can be, for example, actual image intensity differences between the images at the same location on the materials interface 115. Those skilled in the art will recognize that image intensity refers to brightness or darkness and is dependent upon the size of the aperture used. The actual differential can be, for example, image color (or gray scale) differences between the images at the same location on the materials interface 115. The actual differential can be, for example, spectral response differences between the images at the same location on the materials interface 115. Those skilled in the art will recognize that a spectral response pattern refers to the magnitude of energy that an object reflects or emits across a range of wavelengths. Alternatively, the actual differential can be any other suitable measurable differential between the images at the same location on the materials interface 115.

A determination can then be made as to whether or not the materials interface 115 is defective (see process 412). That is, the method can include determining whether the materials interface 115 contains defect(s) at specific location(s). This determination can be made at process 412 (e.g., by the analyzer 103) based on the actual differential and an expected differential stored in the defect library 191.

Specifically, as discussed in detail above, each embodiment 100A-100F of the inspection system can further include a memory 190, which is accessible by the analyzer 190, and a defect library 191, which is stored within the memory 190. The defect library 191 can list multiple interfaces by type and, specifically, by the two materials positioned immediately adjacent to each other at the materials interface. Furthermore, for each interface, the defect library 191 can indicate the following: a particular condition variation used during inspection and an expected differential (if any) in a property of the images of the materials interface 115, which will indicate that the materials interface is non-defective when the inspection is performed using the particular condition variation. The actual differential determined at process 410 can be compared to an expected differential, acquired from the defect library 191, in order to determine whether the materials interface 115 is defective (i.e., whether the materials interface contains any defects) at process 412. When the actual differential and the expected differential are essentially the same across the images, then a determination can be made that the materials interface is non-defective. However, if the actual differential and the expected differential are different (e.g., by some threshold amount) at the same location the images, then a determination can be made that the materials interface contains at that location.

For example, FIGS. 2A and 2B illustrate exemplary images 201 and 202, respectively, of a specific non-defective materials interface (e.g., a non-defective silicon to silicon dioxide interface or any other specific materials interface), wherein the images 201-202 were captured using selectively varied conditions (e.g., a first sub-wavelength aperture (see FIG. 2A) and a second sub-wavelength aperture that is smaller than the first sub-wavelength aperture (see FIG. 2B)) and, as result, the images 201-202 have different image intensity (i.e., brightness) levels. That is, these FIGS. 2A-2B show the expected image intensity level differential between two different images 201-202 of a non-defective materials interface when a particular conditions variation is applied. In this case, the smaller aperture will result in a darker image.

FIGS. 3A and 3B illustrate exemplary images 301 and 302, respectively, of the same materials interface, wherein the images 301-302 were captured using the same selectively varied conditions (e.g., a first sub-wavelength aperture (see FIG. 3A) and a second sub-wavelength aperture that is smaller than the first sub-wavelength aperture (see FIG. 3B)) and, as result, the images 301-302 have different image intensity (i.e., brightness) levels. As illustrated, at one particular location 310 on the materials interface 115 in these images 301-302, the actual differential in the image intensity is significantly different from the expected differential (in this case, much less than expected), thereby indicating a defect at that location 310.

Optionally, at process 412 detected defects can also be identified by type (e.g., void, short, tear, etc.). For example, for each materials interface inspected under a particular conditions variation, the defect library 191 can further associate at least one threshold difference between the expected differential and the actual differential with a specific defect type. In this case, a value of the difference between the expected differential and the actual difference can be determined and compared to the threshold difference in order to identify the defect by type. For example, a particular conditions variation can be a decrease in aperture size by, for example, 50% between the first image and the second image; an expected differential in image intensity between the two images can be, for example, a 50% decrease, and a threshold difference for detecting a void can be, for example, a difference of 10 points or more. In this case, if the actual differential in image intensity between the two images is less than 40%, then a defect can be detected and that defect can be identified as a void.

Optionally, one or more additional inspection processes can be performed using one or more additional inspection device(s) and the results of any additional inspection process can be considered to ensure the accuracy any defect detection and/or identification previously made at process 412 (see process 414 and the inspection system embodiment 100F of FIG. 1F, discussed in greater detail above).

It should be noted that the information, which is stored within the defect library 191 (i.e., information associated with specific materials interfaces and with particular conditions variations used during inspection of those specific materials interfaces) could be empirically determined or, alternatively, determined through simulations. Furthermore, it is anticipated that, as more and more different materials interfaces are inspected under more and more different selectively varied inspection conditions, the defect library 191 will be updated to provide for improved defect detection and identification capabilities.

Finally, in the exemplary method embodiments described above, inspection of only a single materials interface within an object under test is discussed. However, it should be understood that similar techniques may also be used to simultaneously inspect multiple parallel interfaces and/or in multiple intersecting interfaces, particularly when three-dimensional images are captured at process 408.

Also disclosed herein is a computer program product. The computer program product can include a computer readable storage medium having program instructions embodied therewith. The program instructions can be readable by a computer and can cause the computer to perform the above-described method. More particularly, the present invention may be embodied as a system, a method, and/or a computer program product. The computer program product may include a computer readable storage medium (or media)

having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein is an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 5:
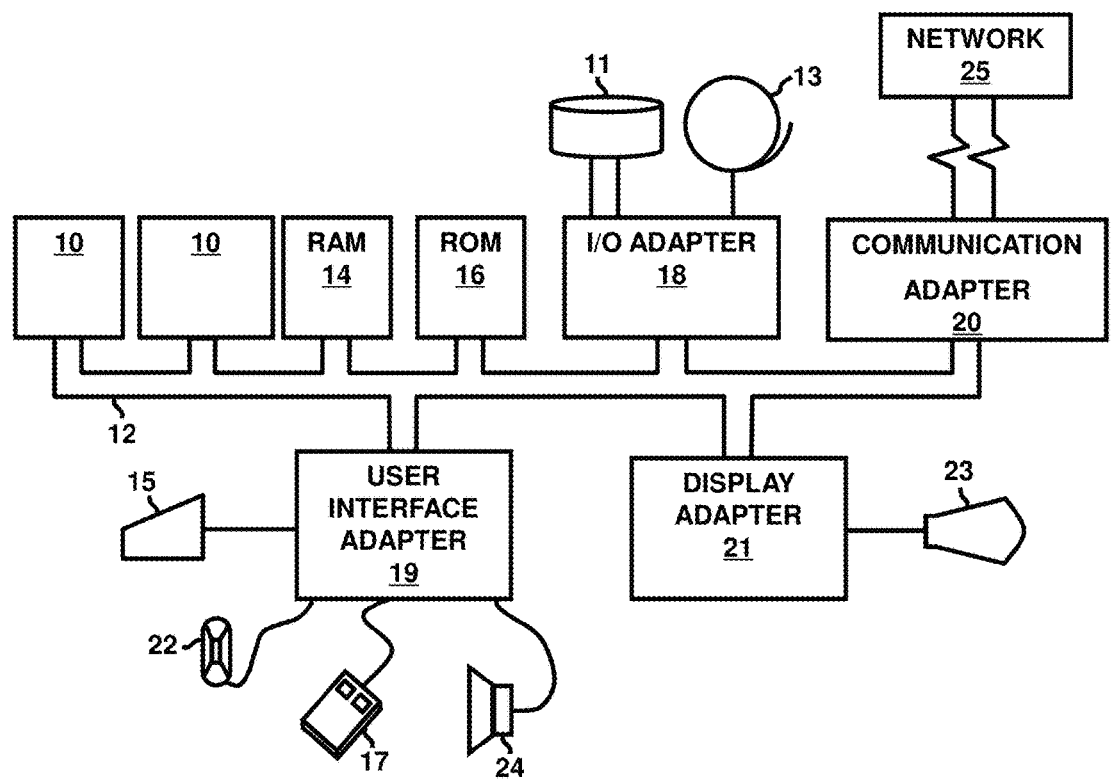
FIG. 5 is a schematic diagram illustrating an exemplary computer system for implementing aspects of the disclosed system, method and computer program product.

A representative hardware environment (i.e., a computer system) for implementing aspects of the disclosed system, method and computer program product embodiments described above is depicted in FIG. 5. This schematic drawing illustrates a hardware configuration of an information handling/computer system in accordance with the embodiments herein. The system includes at least one processor or central processing unit (CPU) 10. The CPUs 10 are interconnected via a system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of the embodiments herein. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

It should be understood that the terminology used herein is for the purpose of describing the disclosed structures and methods and is not intended to be limiting. For example, as used herein, the singular forms "a", "an" and "the" are intended to include the plural forms as well, unless the context clearly indicates otherwise. Additionally, as used herein, the terms "comprises" "comprising", "includes" and/or "including" specify the presence of stated features, integers, steps, operations, elements, and/or components, but do not preclude the presence or addition of one or more other features, integers, steps, operations, elements, components, and/or groups thereof. Furthermore, as used herein, terms such as "right", "left", "vertical", "horizontal", "top", "bottom", "upper", "lower", "under", "below", "underlying", "over", "overlying", "parallel", "perpendicular", etc., are intended to describe relative locations as they are oriented and illustrated in the drawings (unless otherwise indicated) and terms such as "touching", "in direct contact", "abutting", "directly adjacent to", "immediately adjacent to", etc., are intended to indicate that at least one element physically contacts another element (without other elements separating the described elements). The term "laterally" is used herein to describe the relative locations of elements and, more particularly, to indicate that an element is positioned to the side of another element as opposed to above or below the other element, as those elements are oriented and illustrated in the drawings. For example, an element that is positioned laterally adjacent to another element will be beside the other element, an element that is positioned laterally immediately adjacent to another element will be directly beside the other element, and an element that laterally surrounds another element will be adjacent to and border the outer sidewalls of the other element. The corresponding structures, materials, acts, and equivalents of all means or step plus function elements in the claims below are intended to include any structure, material, or act for performing the function in combination with other claimed elements as specifically claimed.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An inspection system comprising:
    a radiation source;
    at least one detector;
    an analyzer; and
    a controller operably connected to the radiation source, the at least one detector and the analyzer,
    wherein the controller controls the radiation source, the at least one detector, and the analyzer during an inspection of an interface between materials of an object under test such that the radiation source illuminates the interface with radiation under selectively varied inspection conditions, such that the at least one detector captures at least two different images of the interface when the interface is illuminated under the selectively varied inspection conditions, and such that the analyzer compares and contrasts the at least two different images to determine an actual differential in at least one property of the images and determines whether the interface is defective, based on the actual differential.

2. The inspection system of claim 1, wherein the selectively varied inspection conditions comprise any of the following:
    different environmental conditions;
    different detector aperture settings;
    different relative locations of any of the radiation source, the at least one detector, and the object;
    different primary beam intensities for the radiation;
    different primary beam frequencies for the radiation; and
    different primary beam directions for radiation.

3. The inspection system of claim 1, wherein the radiation is within any of a terahertz range and a sub-terahertz range.

4. The inspection system of claim 1,
    wherein the object has a first surface and a second surface opposite the first surface,
    wherein the interface is between a first material adjacent to the first surface and a second material adjacent to the second surface,
    wherein beams of the radiation are directed into the first surface, pass through the first material, are reflected off the second material at the interface, and exit back out the first surface, and
    wherein the at least one detector captures the at least two different images from a location adjacent the first surface.

5. The inspection system of claim 1,
    wherein the object has a first surface and a second surface opposite the first surface,
    wherein the interface is between a first material adjacent to the first surface and a second material adjacent to the second surface,
    wherein beams of the radiation are directed into the first surface, pass through the first material, the interface and the second material, and exit out the second surface, and
    wherein the at least one detector captures the at least two different images from a location adjacent the second surface.

6. The inspection system of claim 1,
    wherein the object has a first surface and a second surface opposite the first surface,
    wherein the interface is between a first material adjacent to the first surface and a second material adjacent to the second surface,
    wherein beams of the radiation are directed into the first surface and pass through the first material,
    wherein a first portion of the beams is reflected off the second material at the interface and exits back out the first surface, and wherein a second portion of the beams passes through the interface and the second material and exits out the second surface, wherein the at least one detector comprises a first detector and a second detector, wherein the first detector captures a first image from a first location adjacent the first surface and the second detector captures a second image from a second location adjacent the second surface.

7. The inspection system of claim 1, the analyzer further identifying a defect by type when a determination is made that the interface is defective.

8. The inspection system of claim 1, further comprising a defect library listing multiple interfaces by type and, for each interface, further indicating the following:
   a particular condition variation for the inspection; and
   an expected differential in the property indicating that the interface is non-defective when the inspection is performed using the particular condition variation,
   wherein the defect library is used to determine whether the interface is defective.

9. The inspection system of claim 8, the defect library further indicating a defect type based on a difference between the actual differential and the expected differential.

10. The inspection system of claim 1, the object comprising any of a semiconductor wafer, an integrated circuit chip, an integrated circuit chip package, and a printed circuit board assembly.

11. An inspection method comprising:
   illuminating an interface between materials of an object under test with radiation under selectively varied inspection conditions, wherein the illuminating of the interface is performed using a radiation source of an inspection system;
   capturing at least two different images of the interface when the interface is illuminated under the selectively varied inspection conditions, wherein the capturing of the at least two different images is performed using at least one detector of the inspection system; and
   comparing and contrasting the at least two different images to determine an actual differential in at least one property of the images and, based on the actual differential, determining whether the interface is defective, wherein the comparing and contrasting of the at least two different images and the determining of whether the interface is defective are performed using an analyzer of the inspection system.

12. The inspection method of claim 11, wherein the selectively varied inspection conditions comprise any of the following:
   different environmental conditions;
   different detector aperture settings;
   different relative locations of any of the radiation source, the at least one detector, and the object;
   different primary beam intensities for the radiation;
   different primary beam frequencies for the radiation; and
   different primary beam directions for the radiation.

13. The inspection method of claim 11, wherein the radiation is within any of a terahertz range and a sub-terahertz range.

14. The inspection method of claim 11,
   wherein the object has a first surface and a second surface opposite the first surface,
   wherein the interface is between a first material adjacent to the first surface and a second material adjacent to the second surface,
   wherein beams of the radiation are directed into the first surface, pass through the first material, are reflected off the second material at the interface, and exit back out the first surface, and
   wherein the at least one detector captures the at least two different images from a location adjacent the first surface.

15. The inspection method of claim 11,
   wherein the object has first surface and a second surface opposite the first surface,
   wherein the interface is between a first material adjacent to the first surface and a second material adjacent to the second surface,
   wherein beams of the radiation are directed into the first surface, pass through the first material, the interface and the second material, and exit out the second surface, and
   wherein the at least one detector captures the at least two different images from a location adjacent the second surface.

16. The inspection method of claim 11,
   wherein the object has a first surface and a second surface opposite the first surface,
   wherein the interface is between a first material adjacent to the first surface and a second material adjacent to the second surface,
   wherein beams of the radiation are directed into the first surface and pass through the first material,
   wherein a first portion of the beams is reflected off the second material at the interface and exits back out the first surface, and
   wherein a second portion of the beams passes through the interface and the second material and exits out the second surface,
   wherein the at least one detector comprises a first detector and a second detector, and
   wherein the first detector captures a first image from a first location adjacent the first surface and the second detector captures a second image from a second location adjacent the second surface.

17. The inspection method of claim 11, further comprising identifying, by the analyzer, a defect by type when a determination is made that the interface is defective.

18. The inspection method of claim 11, further comprising:
   generating and storing a defect library, the defect library listing multiple interfaces by type and, for each interface, further indicating the following:
   a particular condition variation for the inspection; and
   an expected differential in the property indicating that the interface is non-defective when the inspection is performed using the particular condition variation,
   wherein the defect library is used to determine whether the interface is defective.

19. The inspection method of claim 18, the defect library further indicating a defect type based on a difference between the actual differential and the expected differential.

20. A non-transitory computer program product comprising a computer readable storage medium having program instructions embodied therewith, the program instructions being readable by a computer and causing the computer to perform a method, the method comprising:
   causing a radiation source of an inspection system to illuminate an interface between materials of an object under test with radiation under selectively varied inspection conditions;

causing at least one detector of the inspection system to capture at least two different images of the interface when the interface is illuminated under the selectively varied inspection conditions; and causing an analyzer of the inspection system to compare and contrast the at least two different images to determine an actual differential in a property of the images and to further determine whether the interface is defective, based on the actual differential.

\* \* \* \* \*